(12) United States Patent
Chen et al.

(10) Patent No.: US 7,571,637 B2
(45) Date of Patent: Aug. 11, 2009

(54) DESIGN STRUCTURE FOR AN ON-CHIP REAL-TIME MOISTURE SENSOR FOR AND METHOD OF DETECTING MOISTURE INGRESS IN AN INTEGRATED CIRCUIT CHIP

(75) Inventors: Fen Chen, Williston, VT (US); Kai D. Feng, Hopewell Junction, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 11/926,241

(22) Filed: Oct. 29, 2007

(65) Prior Publication Data

US 2009/0107220 A1    Apr. 30, 2009

(51) Int. Cl.
*G01N 5/02* (2006.01)
(52) U.S. Cl. .......................................... 73/73
(58) Field of Classification Search ................ 73/73
See application file for complete search history.

(56) References Cited

U.S. PATENT DOCUMENTS

| | | | |
|---|---|---|---|
| 3,943,557 A | | 3/1976 | Frazee et al. |
| 4,057,823 A | | 11/1977 | Burkhardt et al. |
| 4,224,565 A | | 9/1980 | Sosniak et al. |
| 4,356,641 A | | 11/1982 | Rosenau |
| 4,638,346 A | | 1/1987 | Inami et al. |
| 4,684,884 A | | 8/1987 | Soderlund |
| 4,775,831 A | | 10/1988 | Annamalai |
| 4,902,961 A | * | 2/1990 | De et al. .................... 324/640 |
| 5,606,264 A | | 2/1997 | Licari et al. |
| 6,202,479 B1 | * | 3/2001 | Frybarger ..................... 73/73 |
| 6,445,565 B1 | | 9/2002 | Toyoda et al. |
| 6,580,600 B2 | | 6/2003 | Toyoda et al. |
| 6,629,057 B2 | * | 9/2003 | Zweig et al. ................ 702/182 |
| 6,885,201 B2 | * | 4/2005 | Germiquet et al. .......... 324/663 |
| 7,032,448 B2 | | 4/2006 | Hamamoto |
| 2002/0141136 A1 | | 10/2002 | Toyoda et al. |
| 2005/0271403 A1 | * | 12/2005 | Kaneko et al. ................ 399/44 |
| 2006/0190917 A1 | * | 8/2006 | Edwards ....................... 716/21 |
| 2008/0115569 A1 | * | 5/2008 | Gally et al. .................... 73/73 |

FOREIGN PATENT DOCUMENTS

JP    11-017230    1/1999

OTHER PUBLICATIONS

Richard K. Traeger, "Nonhermeticity of Polymeric Lid Sealants," IEEE Transactions on Pars, Hybrids, and Packaging, vol. PHP-13, No. 2, Jun. 1977, pp. 147-152.
C. Azeredo Leme, T. Boltshauser and H. Baltes, "CMOS Absolute Value Precision Capacitance Measurement System," 0-7803-0593-0/92, IEEE, pp. 1277-1279.
S.V. Silverthorne, C.W. Watson, R.D. Baxter, "Integrated Relative Humidity Sensor," TH-215-4/88/0000-0067, 1988, IEEE, pp. 67-71.
U.S. Appl. No. 11/672,535, filed Feb. 8, 2007, entitled "On-Chip Real-Time Moisture Sensor For and Method of Detecting Moisture Ingress in an Integrated Circuit Chip," Fen Chen, Kai D. Feng.
First Office Action dated Dec. 17, 2008 regarding related U.S. Appl. No. 11/672,535.
Response to First Office Action dated Mar. 17, 2009, regarding related U.S. Appl. No. 11/672,535.
Terminal Disclaimer dated Mar. 17, 2009, regarding related U.S. Appl. No. 11/672,535.

* cited by examiner

*Primary Examiner*—Hezron Williams
*Assistant Examiner*—Gunnar J Gissel
(74) *Attorney, Agent, or Firm*—Downs Rachlin Martin PLLC

(57) ABSTRACT

A design structure for an on-chip real-time moisture detection circuitry for monitoring ingress of moisture into an integrated circuit chip during the operational lifetime of the chip. The moisture detection circuitry includes one or more moisture-sensing units and a common moisture monitor for monitoring the state of each moisture-sensing units. The moisture monitor can be configured to provided a real-time moisture-detected signal for signaling that moisture ingress into the integrated circuit chip has occurred.

5 Claims, 8 Drawing Sheets

DESIGN STRUCTURE FOR AN ON-CHIP REAL-TIME MOISTURE SENSOR FOR AND METHOD OF DETECTING MOISTURE INGRESS IN AN INTEGRATED CIRCUIT CHIP

FIELD OF THE DISCLOSURE

The present disclosure generally relates to the field of moisture detection in an integrated circuit. In particular, the present disclosure is directed to a design structure for an on-chip real-time moisture sensor for and method of detecting moisture ingress in an integrated circuit chip.

BACKGROUND

The ingress of moisture into an integrated circuit (IC) chip can have a negative impact on the performance and reliability of circuitry aboard the chip. When moisture ingresses into the active chip circuitry, both the performance and reliability of IC chip significantly degrades. Severe moisture penetration can cause significant failures in the operation of the IC chip.

One method utilized today for detecting moisture in integrated circuits is a gas detection operation, which is performed during the manufacturing test and packaging stage of the IC fabrication process. However, this gas detection operation uses off-chip mechanisms and, thus, it does not provide a on-chip moisture detection scheme for the IC when it is installed in a finished product and operating in the field. During the lifetime of an IC chip, the package may crack because of, for example, severe temperature changes and other mechanical stress factors that can cause the chip moisture seal to break. If the chip seal breaks, moisture ingression into the chip may occur, which can result in IC chip malfunction and/or failure.

This may be especially true for large packaged integrated circuits used in severe temperature environments, such as IC chips for automobile, aircraft, and spacecraft applications. Additionally, because of advances in IC technology there may be increased current leakage and increased integration density of the circuits and, thus, much heat may be generated in an integrated circuit system. In particular, the temperature of the IC package may be ramped from room temperature to higher than 100° C. The large swing in temperature may cause tiny cracks in the IC package and in the die cover layer. These cracks may allow moisture invasion that leads to degradation of the IC chip performance and reliability.

SUMMARY OF THE DISCLOSURE

In one embodiment a design structure embodied in a machine readable medium used in a design process for an integrated circuit chip is provided. The design structure includes functional circuitry; and moisture-detecting circuitry that includes: a moisture-sensing unit for generating a sense signal that varies as a function of moisture within the moisture-sensing unit; and a moisture monitor in electrical communication with the moisture-sensing unit, the moisture monitor including: a memory for storing a first value, the first value stored in the memory at a first time; and a comparator for comparing a second value of the sense signal to the first value, the second value being provided by the moisture-sensing unit subsequent to the first value being stored in the memory.

In another embodiment, a design structure embodied in a computer readable medium for performing a method of detecting ingress of moisture into an integrated circuit chip is provided. The design structure includes a means for storing a first value in a memory of the integrated circuit chip; a means for generating, aboard the integrated circuit chip, a second value of the sense signal to the first value; and a means for generating a warning if the second value is lower than the first value by a predetermined amount.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

Figure 1:
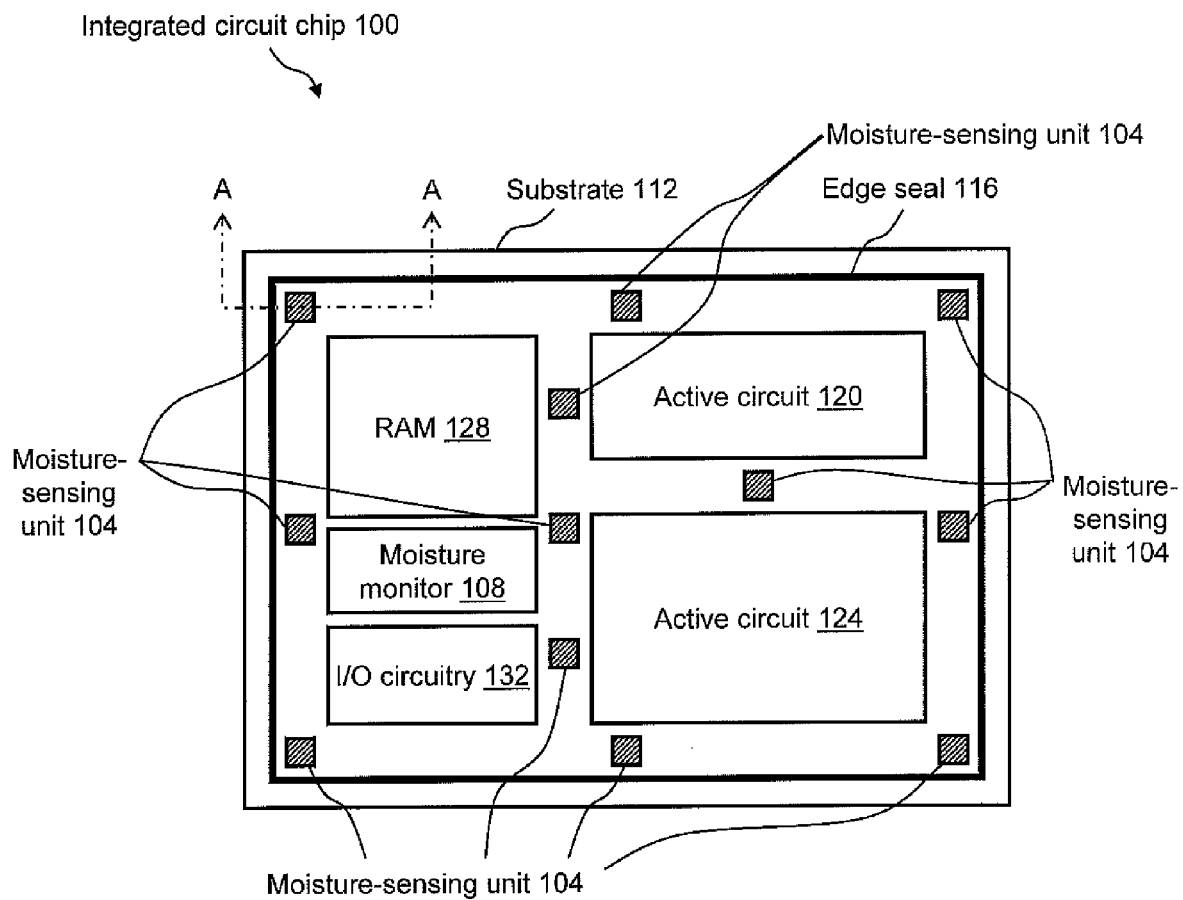
FIG. 1 is a high-level schematic diagram of an example of an integrated circuit chip that includes a plurality of moisture-sensing units.

The present invention is directed to a design structure for an on-chip real-time moisture sensor for and method of detecting moisture ingress in an integrated circuit chip. Referring now to the drawings, FIG. 1 shows an integrated circuit (IC) chip 100 that includes one or more moisture-sensing units 104 and a moisture monitor 108 each made in accordance with the present invention. As described below in detail, moisture sensing units 104, in conjunction with moisture monitor 108, can sense the ingress of moisture into IC chip 100 and respond to the detection of moisture in a predetermined way, e.g., by providing a user of the IC chip or product incorporating the IC chip with a warning or other information concerning the detected moisture and/or providing information to other circuitry aboard IC chip that may allow the other circuitry to take appropriate action, to name a few. As those skilled in the art will appreciate, IC chip 100 may include, for example, a conventional silicon substrate 112, around the peripheral edge of which may be an edge seal 116. Edge seal 116 may be formed of an electrically conductive material, such as, but not limited to, aluminum, copper, and alloys of these materials. Located within the boundary defined by edge seal 116, IC chip 100 may include one or more regions of active circuitry, such as, but not limited to, an active circuit 120, an active circuit 124, memory 128, e.g., RAM, and input/output (I/O) circuitry 132. For reasons discussed below, if more than one moisture-sensing unit 104 is provided, they may be installed in a distributed fashion within the area of the active circuitry bounded by edge seal 116. For example, one or more of a plurality of moisture-sensing units 104 may be installed around the peripheral edge of IC chip 100 in close proximity to edge seal 116 and one or more others of the moisture-sensing units may be installed in the gaps between regions of circuitries 120, 124, 128, 132, 108. Of course, the arrangement of moisture sensing units 104 shown in FIG. 1 is merely exemplary. Many other arrangements are possible, as those skilled in the art will certainly appreciate.

Figure 2:
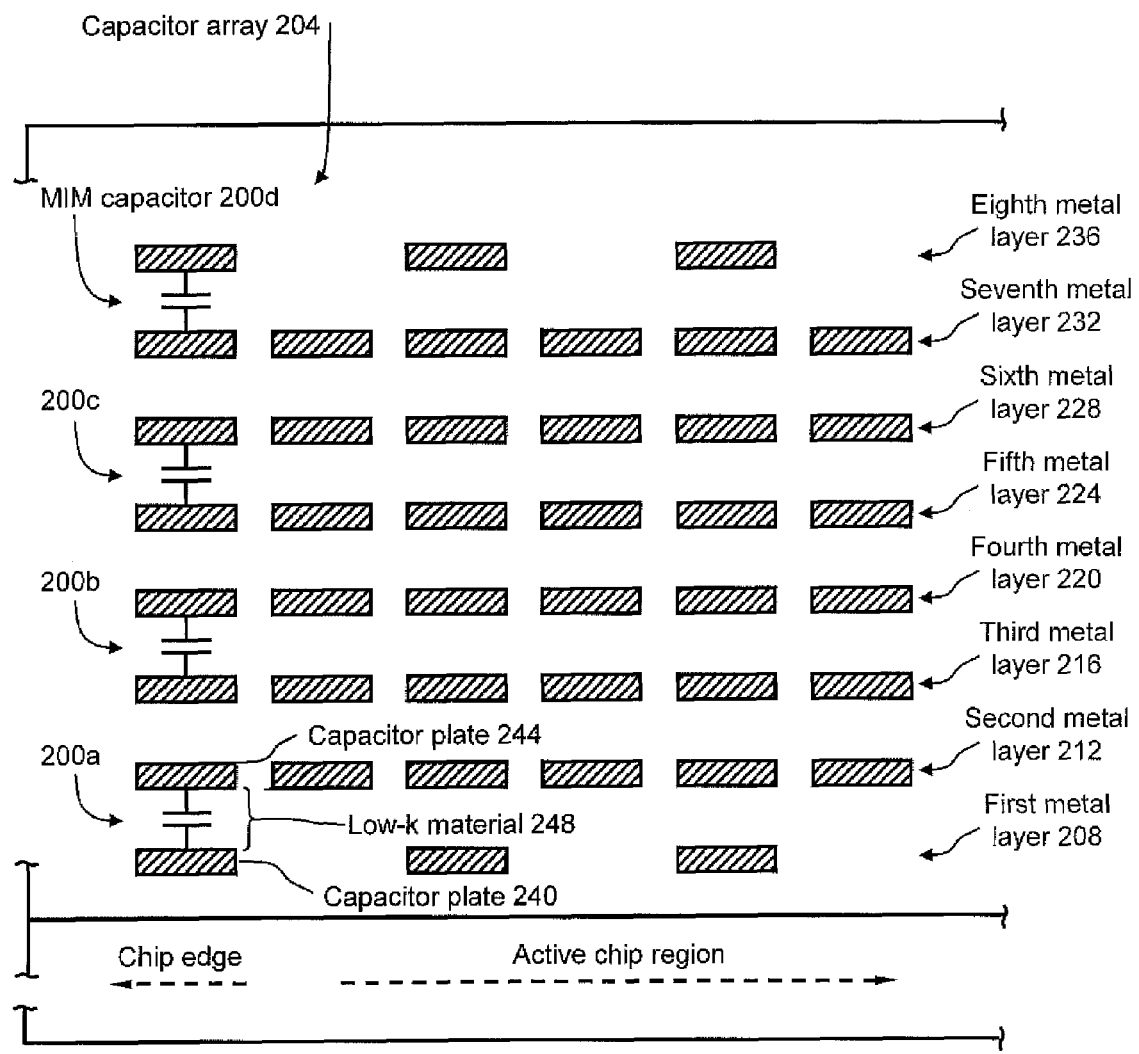
FIG. 2 is a schematic cross-sectional view, taken along line A-A of FIG. 1, of an example capacitor array formed among the metal layers of the integrated circuit chip of FIG. 1 that is suitable for use in the moisture-sensing units aboard the integrated circuit chip.

Each moisture-sensing unit 104 may include an active device that has at least one measurable electrical characteristic that changes as a function of the moisture level of its environment. In one example, each moisture-sensing unit 104 may include a low-k capacitor, such as, but not limited to a metal-insulator-metal (MIM) capacitor, e.g., a copper/low-k (Cu/low-k) capacitor, as shown in FIG. 2 as elements 200a-d, and a low-k vertical natural capacitor (VNCAP), as shown as element 300 in FIG. 3. Referring to FIG. 2, and also to FIG. 1, an array 204 of low-k MIM capacitors 200a-d may be formed among the metal layers, here metal layers 208, 212, 216, 220, 224, 228, 232, 236, of IC chip 100, to take advantage of these layers, which are needed regardless of whether or not the IC chip is provided with moisture-sensing circuit units 104 (FIG. 1) and moisture monitor 108 (FIG. 1). In this example, MIM capacitor 200a includes one charge plate 240 formed on first metal layer 208 and another charge plate 244 formed on second metal layer 212, with a quantity of low-k material 248 disposed therebetween. MIM capacitors 200b-d are formed in a similar manner between, respectively, third and fourth metal layers 216, 220, fifth and sixth metal layers 224, 228 and seventh and eighth metal layers 232, 236. Each of these MIM capacitors 200a-d may form a corresponding respective part of moisture-sensing units 104, as discussed in more detail below. The example capacitor scheme of capacitor array 204 of FIG. 2 provides a vertical configuration of MIM capacitors 200a-d for monitoring moisture penetration along edge seal 116 (FIG. 1).

Figure 3:
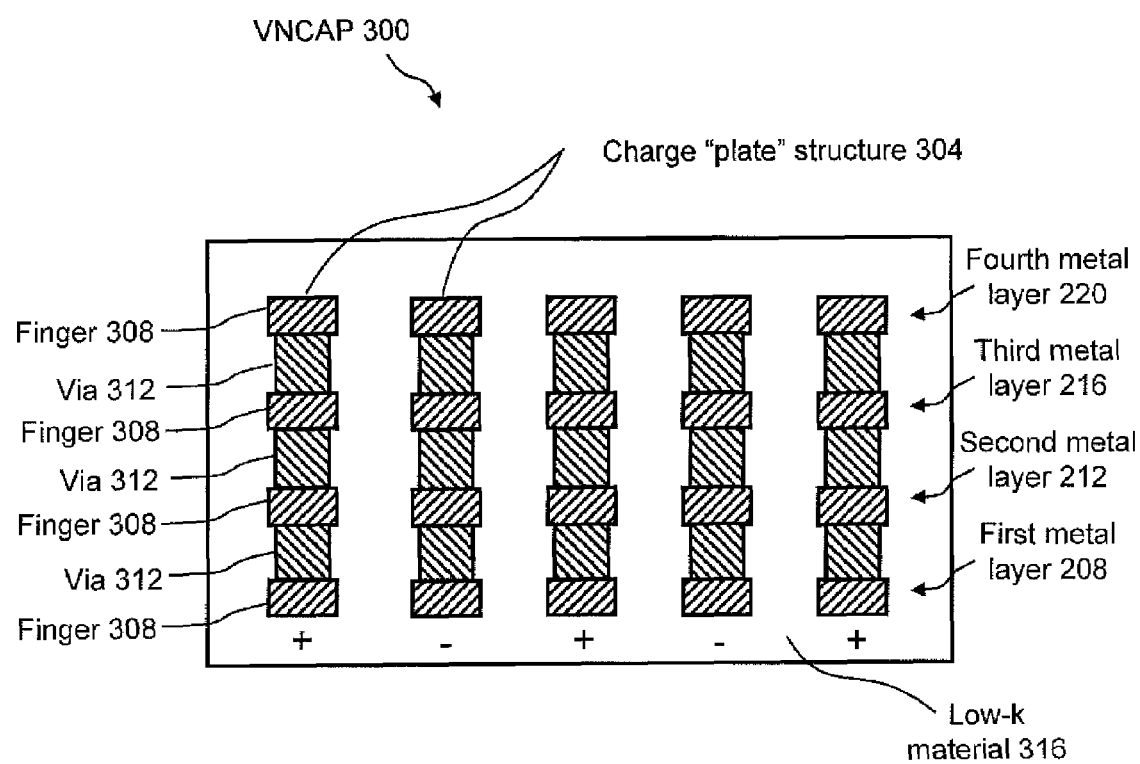
FIG. 3 is a cross-sectional view of another example of a capacitor that is suitable for use in a moisture-sensing units of an integrated circuit.

As mentioned above, in addition to utilizing MIM capacitors, such as MIM capacitors 200a-d, one or more of moisture-sensing units 104 (FIG. 1) may each include one or more VNCAPs, such as VNCAP 300 of FIG. 3. Referring to FIG. 3, VNCAP 300 may be formed among the back-end-of-the-line metal layers, e.g., first through fourth metal layers 208, 212, 216, 220, at any region of these layers that is not otherwise occupied by other structures, such as the wires (not shown) on these layers. VNCAP may comprise a plurality of charge "plate" structures 304 that each include conductive fingers 308 on corresponding respective metal layers 208, 212, 216, 220 and conductive vias 312 that electrically connect together the fingers on adjacent layers. Not shown, but present, are conductor strips on each metal layer 208, 212, 216, 220 that electrically connect like-polarity ones of charge plate structures 304 together. The resulting structure is a dual-comb structure in which opposite polarity charge plate structures 304 are interdigitated with one another. Entire VNCAP 300 is encased in a low-k material 316, such as a low-k SiCOH, which has a dielectric constant (k) of about 3.0. A benefit of using a VNCAP, such as VNCAP 300, is that it can be placed in any "empty" space among the metal layers without the need for any additional mask levels. This result in a relatively low cost for implementing VNCAPs of moisture-sensing units 104 and providing a 3D moisture detection for all the metal levels.

A low-k capacitor, such as each of MIM capacitors 200a-d (FIG. 2) or VNCAP 300 (FIG. 3), may include a dielectric film having a low dielectric constant (k) and is sensitive to moisture. In particular, moisture has two effects on a low-k capacitor. First, as moisture increases the effective capacitor dielectric constant (k) increases due to the very high dielectric constant of water and, thus, the capacitance increases. Second, as moisture increases the leakage current of the capacitor increases, which is equivalent to adding a resistor in parallel to the capacitor and, thus, the real charging current is reduced. Consequently, the capacitance of a low-k capacitor typically changes as a function of moisture level as indicated via a change in the stored voltage Vc thereon, which is measurable.

Referring again to FIG. 1, moisture monitor 108 may be configured to monitor the states of all moisture-sensing units 104 aboard IC chip and generate a moisture-warning or other moisture-detected signal when moisture ingression is detected and reaches a certain predetermined level as indicated via one or more of the moisture-sensing units. A user of IC chip 100, the product into which the IC chip is incorporated and/or other circuitry(ies) aboard the IC chip itself may select any appropriate response to the moisture warning from moisture monitor 108. Example responses to the moisture detection signal of moisture monitor 108 may include, but are not limited to, prompting data to be backed up, prompting the operations of the active circuitry to cease within a certain amount of time, providing the user a core circuitry "risk of failure" assessment (e.g., 50% risk of failure), providing the user an estimated core circuitry "time to failure" in order to determine certain operations to execute according to the estimated time remaining, and any combinations thereof. More details of example moisture-sensing units and moisture monitors are described with reference to FIGS. 4, 5, 6, and 7.

Figure 4:
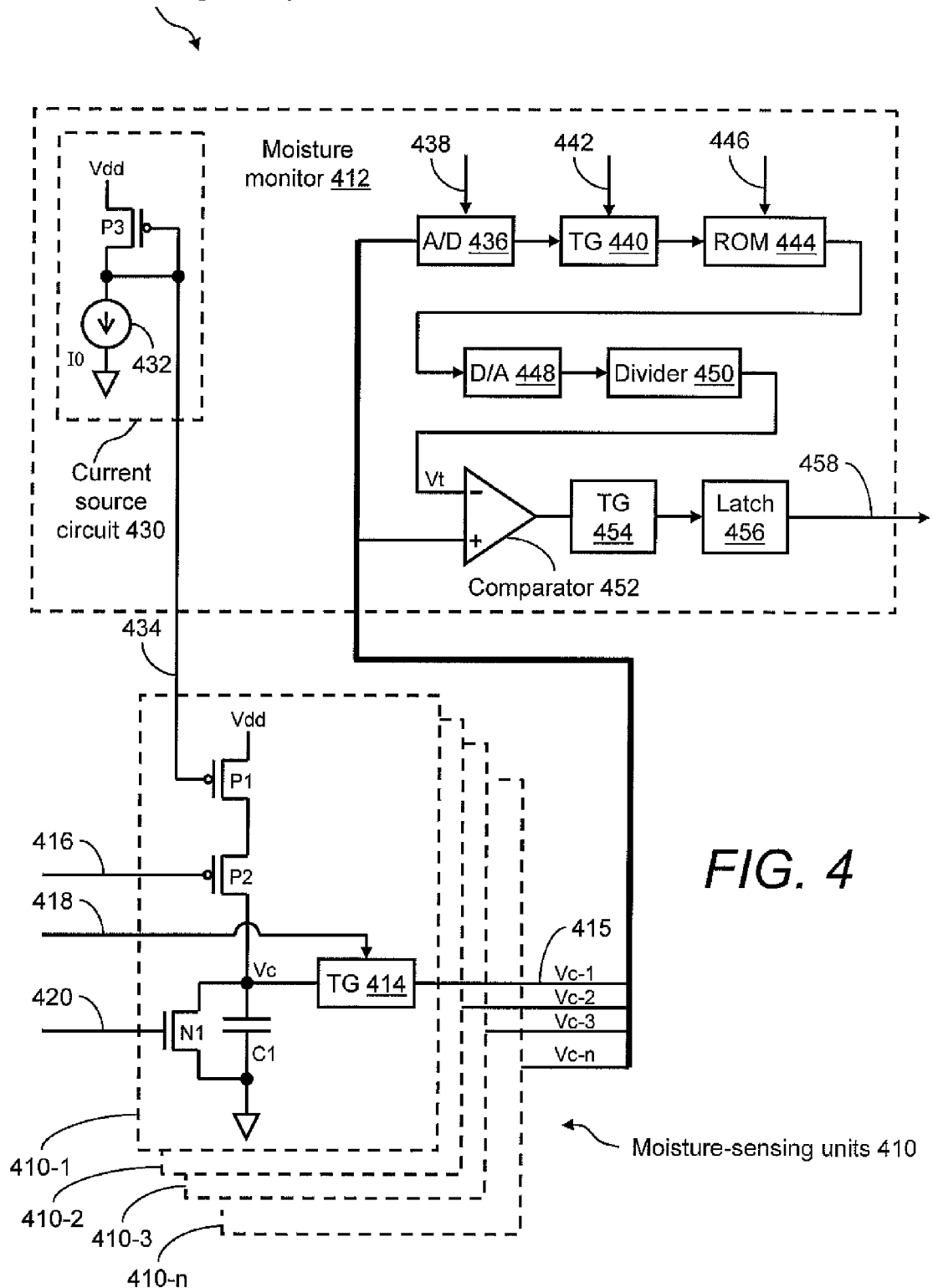
FIG. 4 is a schematic diagram of an example of moisture-detecting circuitry for providing a residual lifetime warning mechanism in an integrated circuit chip.

FIG. 4 illustrates a schematic diagram of moisture-detecting circuitry 400, which is an example of moisture-detecting circuitry for providing a residual lifetime warning mechanism in an IC chip (not shown) that may be the same as or similar to IC chip depicted in FIG. 1. In this example, moisture-detecting circuitry 400 provides a single level of moisture warning. Moisture-detecting circuitry 400 may include one or more moisture-sensing units 410 and a moisture monitor 412 for monitoring the states of the one or more moisture-sensing units 410. In one example, moisture-detecting circuitry 400 may include moisture-sensing units 410-1 through 410-n, as illustrated in FIG. 4.

Each moisture-sensing unit 410 may include one or more moisture sensitive elements, such as a low-k capacitor C1, which may be, for example, a Cu/low-k MIM capacitor (e.g., any one of MIM capacitors 200a-d of FIG. 2) or a low-k VNCAP (e.g., VNCAP 300 of FIG. 3). Capacitor C1 may be electrically connected between a voltage node Vc and ground. Connected in parallel with capacitor C1 between voltage node Vc and ground may be a first switching device, such as an n-type field-effect transistor (FET) N1. Two additional switching devices, such as p-type FET P1 and a p-type FET P2, are connected in series between a power supply, such as Vdd or Vcc, and voltage node Vc. Additionally, a transmission gate (TG) 414, which may be a pass transistor, is connected to voltage node Vc and is a control mechanism for passing a Vc sense signal 415, which reflects the voltage Vc across capacitor C1 that varies as a function of moisture level, to moisture monitor 412. Each moisture-sensing unit 410 may include a plurality of control signals controlling the operation and enabling the output thereof.

More particularly, FETs P1, P3 form a current mirror. FET P1 may be controlled via a control signal 434 from moisture monitor 412 and is the charging current source device of moisture-sensing unit 410. FET P2 is controlled via a control signal 416. When FET P2 is turned on, capacitor C1 is charged and a voltage, which is measurable, is developed at voltage node Vc. A control signal 418 may be used to activate TG 414, which allows the voltage at voltage node Vc (e.g., the Vc sense signal 415) to be passed to moisture monitor 412. FET N1 is controlled via a control signal 420. When FET N1 is turned on as a reset, capacitor C1 is discharged and the voltage at voltage node Vc falls to about ground (about 0.0 volts). FET N1 and FET P2 are not turned on at the same time. Each respective moisture-sensing unit 410 have a unique set of control signals 416, 418, and 420, and each provide a unique Vc sense signal 415 to moisture monitor 412 via each respective TG 414. Control signals 416, 418, and 420 for each moisture-sensing unit 410 are supplied by an internal or external controller or processor (not shown) that is associated with the IC chip upon which moisture-detecting circuitry 400 is installed.

In this example, a core element of the moisture sensor circuitry of each moisture-sensing unit 410 is low-k capacitor C1. When capacitor C1 is charged by a current pulse, the voltage on voltage node Vc across the capacitor C1 approximately equals $(I \times T)/C$; where I is the charging current, T is the pulse duration (e.g., provided at control signal 416 at FET P2), and C is the capacitance of capacitor C1. In one example, the selections of I, T and C usually follows up the formula of $(I \times T)/C = 0.5\ Vdd$ to $0.75\ Vdd$. Moisture ingression increases the leakage paths and film polarization, which results in an increased leakage current and film k-value that is reflected by an increased capacitance value. When the moisture penetrates into the IC chip, the voltage across capacitor C1, here voltage Vc, may decrease because of the following two factors: (1) as moisture increases, the effective capacitor dielectric constant (k) increases and, thus, the capacitance increases and (2) as moisture increases, the leakage current of the capacitor increases, which is equivalent to adding a resistor in parallel to the capacitor and, thus, the real charging current is reduced.

Moisture monitor 412 may include a current source circuit 430 that provides the control signal 434 that is common to all moisture-sensing units 410 of moisture-detecting circuitry 400. Current source circuit 430 may be formed of a p-type FET P3 and a constant current source 432 that may be connected in series between the power supply and ground. Constant current source 432 supplies a constant current I0. In one example, constant current source 432 may be a FET device that is controlled to provide a constant current. FET P3 of current source circuit 430 and FET P1 of each moisture-sensing unit 410 form a current mirror scheme that has a current ratio of K for supplying a constant current as a function of current I0 to each moisture-sensing unit 410.

Moisture monitor 412 may further include an analog-to-digital converter (A/D) 436. The input of A/D 436 may be the Vc-1 through Vc-n sense signals 415 of the respective moisture-sensing units 410-1 through 410-n, which are electrically connected together, but only one of which is activated at any given time. A control signal 438 is provided for sampling A/D 436, which performs an analog-to-digital conversion operation for receiving an analog input voltage and generating a digital equivalent thereof. The output of A/D 436 feeds an input of a TG 440 that is controlled via a control signal 442. TG 440 may be, for example, a pass transistor. An output of TG 440 feeds an input of an on-chip storage device, such as a read only memory (ROM) 444. A set of control signals 446 are provided to ROM 444 for providing addressing thereto and read control thereof. The storage capacity of ROM 444 is at least suitable for storing a unique Vc value for each moisture-sensing unit 410 within moisture-detecting circuitry 400.

In one example, ROM 444 may be a TaN resistor-based read only memory as described with reference to U.S. patent application Ser. No. 11/161,332, entitled, "Phase-change TaN resistor based triple-state/multi-state read only memory." Each moisture-sensing unit 410 is assigned an address within ROM 444. In one example, when there are ten moisture-sensing units 410 within moisture-detecting circuitry 400, ROM 444 contains at least ten unique storage locations. Control signals 438, 442, 446 for moisture monitor 412 are supplied by an internal or external controller or processor (not shown) that is associated with the integrated circuit upon which moisture-detecting circuitry 400 is installed.

ROM 444 supplies a digital output of one or more bits to a digital-to-analog converter (D/A) 448, which performs a digital-to-analog conversion operation for receiving a digital input and generating an analog voltage equivalent thereof. An output of D/A 448 feeds an input of a divider 450, which may be voltage divider circuit for generating any user-defined fraction of its input voltage. Divider 450 may provide a divide ratio according to Monte Carlo simulation results to set a margin in order to avoid false alarm. In one example, the output of divider 450 may be 95% of its input voltage value that is supplied by D/A 448. The combination of D/A 448 and divider 450 provides a threshold voltage Vt to which the Vc-1 through Vc-n sense signals 415 of moisture-sensing units 410-1 through 410-n, respectively, are compared.

A comparator 452, which may be a standard analog voltage comparator device, may be provided within moisture monitor 412 for comparing the Vc-1 through Vc-n sense signals 415 of moisture-sensing units 410-1 through 410-n, respectively, to the threshold voltage Vt from divider 450. The output of comparator 452 feeds a TG 452, which may be a pass transistor, that provides a logic one or zero to an input of a latch 456. Latch 456 may be a clocked latch for storing the moisture warning status of moisture-detecting circuitry 400 and generating a moisture-detected signal 458. Latch 456 may be a single bit latch for reading one at a time the moisture warning status of each moisture-sensing unit 410. Alternatively, latch 456 may be a multi-bit register for capturing the moisture warning status of all moisture-sensing units 410, which may be read in parallel, and wherein each bit corresponds to a corresponding respective one of moisture-sensing units 410. Latch 456 may be fed by a clock signal (not shown) and reset signal (not shown).

The operation of moisture detecting circuitry, such as moisture detecting circuitry 400, for detecting ingress of moisture into an integrated circuit chip may be as follows. For each moisture-sensing unit 410, at the beginning of a chip power-up process and when the chip is dry and undamaged, each FET N1 of each moisture-sensing unit 410 is turned on via each respective signal 420 and capacitor C1 is discharged and, thus, voltage node Vc of each moisture-sensing unit 410 may be set to around ground (i.e., to around 0.0 volts). Additionally, all the bits of latch 456 may be reset to a state that is defined as a "normal" state. For example, the moisture alarm is not active when moisture-detected signal 458 of latch 456 is a high logic state. Subsequently, a pulse that has an accurate pulse width of T is applied to the gate of each FET P2 of each moisture-sensing unit 410 via each respective signal 416. In doing so, each FET P2 of each moisture-sensing unit 410 is turned on and each respective capacitor C1, which is the moisture sensor, is charged with (K×current I0) for the time period of T and each respective voltage node Vc is at a certain voltage level. At the completion of this operation, each capacitor C1 of each moisture-sensing unit 410 is in a charged state and the voltage at each voltage node Vc reflects the condition of each capacitor C1 in a dry and undamaged condition, which may be a reference Vc value.

Subsequently, the Vc value of capacitor C1 of each moisture-sensing unit 410 is converted to the digital data by the analog to digital converter A/D 436 and the digital data are stored within ROM 444 as a reference Vc value for that moisture-sensing unit when the IC chip is in a dry and undamaged condition (e.g., reference Vc value may be stored prior to deploying the integrated circuit chip into in-situ operation). In particular, the voltage value at Vc sense signal 415 of each moisture-sensing unit 410 is stored one at a time within ROM 444. More specifically, TG 414 of the selected moisture-sensing unit 410 may be turned on via its respective signal 418 and, thus, the Vc sense signal 415 of the selected moisture-sensing unit 410 is presented at the input of A/D 436 of moisture monitor 412. A trigger signal 438 may be applied to A/D 436, which initiates the analog-to-digital conversion operation and then the control signal 442 may be applied to TG 440, which transmits the output of A/D 436 to ROM 444. The output of A/D 436 is then stored in one location of ROM 444 that is defined by control signals 446 of ROM 444. The data (e.g., corresponding to each Vc sense signal 415) that is stored in ROM 444 serves as a reference Vc value for a later moisture detection operation.

For example, in a periodic moisture detection operation (e.g., after the IC chip has been deployed into in-situ operation), comparator 452 compares an actual real-time voltage Vc (i.e., an actual Vc voltage that may be a function of moisture that is present in the IC chip) of a selected moisture-sensing unit 410 to voltage Vt of divider 450, which is the stored reference Vc value for the selected moisture-sensing unit 410 minus a certain voltage margin. When the actual voltage Vc is higher than voltage Vt, the output of comparator 452 may be, for example, at a certain state, such as a logic high, which may be the "normal" state. However, when voltage Vc is lower than voltage Vt, the output of comparator 452 may be, for example, at a logic low. In both cases, TG 454 transmits the logic signal from comparator 452 to latch 456 which reflects the moisture status of the given moisture-sensing unit 410. In the case wherein the actual Vc voltage of a given moisture-sensing unit 410 falls below the voltage Vt at comparator 452, moisture-detected signal 458 of latch 456 may be set to a logic low, in effect generating a moisture alarm. The bits of latch 456 correspond to the respective moisture-sensing unit 410 that are installed at different locations of the chip. The time difference from the initial use of the integrated circuit in the field to when a moisture alarm is detected at moisture-detected signal 458 of latch 456 may indicate the moisture ingression speed. As seen, moisture-detecting circuitry 400 provides a single level of moisture warning that is based on an analog comparison of one or more actual voltage Vc values to a single threshold voltage Vt. However, in other embodiments, moisture-detecting circuitry may be configured to provide multiple levels of moisture warning, as exemplified in FIG. 5.

Figure 5:
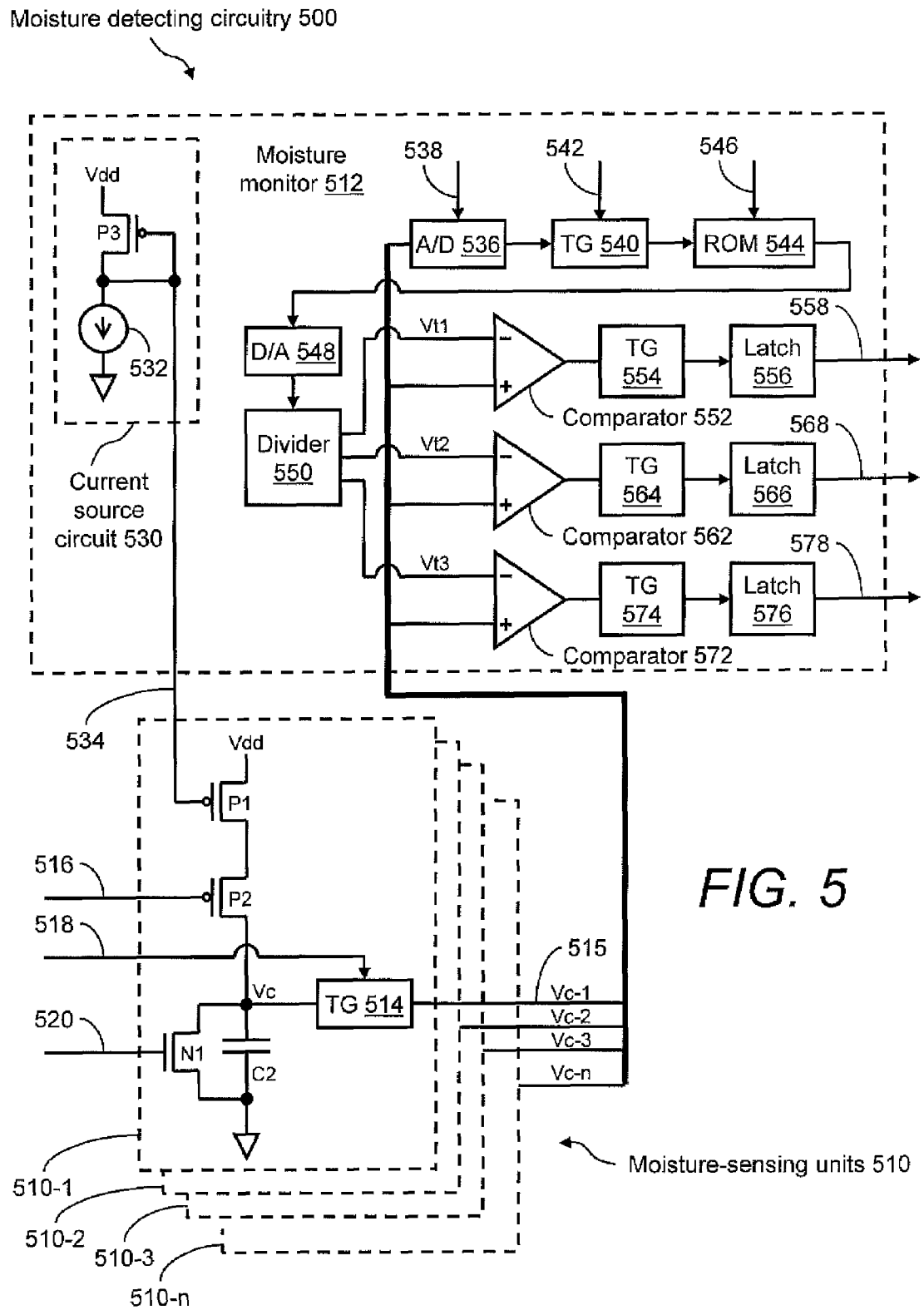
FIG. 5 is a schematic diagram of another example of moisture-detecting circuitry for providing a residual lifetime warning mechanism in an integrated circuit chip.

FIG. 5 illustrates moisture-detecting circuitry 500 that is another example of moisture-detecting circuitry for providing a residual lifetime warning mechanism in an integrated circuit chip. However, in this example moisture-detecting circuitry 500 provides multiple levels of moisture warning. Moisture-detecting circuitry 500 may include one or more moisture-sensing units 510 and a moisture monitor 512 for monitoring the states of the one or more moisture-sensing units 510. In one example, moisture-detecting circuitry 500 may include moisture-sensing units 510-1 through 510-n, as illustrated in FIG. 5.

The one or more moisture-sensing units 510 of FIG. 5 may be substantially the same as the one or more moisture-sensing units 410 of moisture-detecting circuitry 400 of FIG. 4, wherein each includes a moisture sensing element, such as a capacitor C2, and generates a Vc sense signal 515 that is provided to moisture monitor 512 for monitoring the moisture-sensing units for the sensing of moisture. A current source circuit 530, an A/D 536, a TG 540, a ROM 544, and a D/A 548 of moisture monitor 512 may be the same as or similar to, respectively, current source circuit 430, A/D 436, TG 440, ROM 444, and D/A 448 of moisture monitor 412 of FIG. 4. However, and differing from divider 450 of moisture-detecting circuitry 400 that provides a single threshold voltage, moisture-detecting circuitry 500 may include a divider 550 that provides multiple fractions of its input voltage (the stored Vc reference voltage from ROM 544 via D/A 548) for providing multiple threshold voltages to which a selected Vc sense signal 515 may be compared. In one example, divider 550 provides three fractions of the selected Vc reference voltage, by which each value has a unique significance as to the presence of moisture in a corresponding IC chip (not shown). For example, a voltage Vt1 may be 97% of the selected Vc reference voltage and may correspond to a lowest level moisture warning, a voltage Vt2 may be 95% of the selected Vc reference voltage and may correspond to a moderate level moisture warning, and a voltage Vt3 may be 93% of the selected Vc reference voltage and may correspond to a highest level moisture warning.

Voltage Vt1 may feed a corresponding comparator 552, voltage Vt2 may feed a corresponding comparator 562, and voltage Vt3 may feed a corresponding comparator 572. Comparators 552, 562, and 572 are also fed by the selected Vc sense signal 515, as shown in FIG. 5. Additionally, comparators 554, 564, and 574 feed a TG 554, 564, and 574, respectively, that feed a latch 556, 566, and 576, respectively, that generate a moisture-detected signal 558, 568, 578, respectively. In one example, when moisture-detected signal 558 is active a lowest level moisture alarm may be present, when moisture-detected signal 568 is active a moderate level moisture alarm may be present, and when moisture-detected signal 578 is active a highest level moisture alarm may be present. Each comparator 554, 564, and 574 may be substantially the same as comparator 452 of moisture-detecting circuitry 400 of FIG. 4. Each TG 554, 564, and 574 may be substantially the same as TG 454 of moisture-detecting circuitry 400 of FIG. 4. Each latch 556, 566, and 576 may be substantially the same as latch 456 of moisture-detecting circuitry 400 of FIG. 4.

The operation of moisture-detecting circuitry 500 of FIG. 5 is substantially the same as that of moisture-detecting circuitry 400 of FIG. 4, except for the generation of multiple warning levels to which multiple and/or different responses may occur. In particular, an initial set of reference Vc values are stored in ROM 544 to which the actual Vc values (e.g., via Vc sense signals 515) of moisture-sensing units 510-1 through 510-n are compared in a later moisture detection operation. Example responsive actions to the multiple warning levels may be included, but are not limited to, ignoring moisture ingression, starting an on-chip heater (not shown) or other preventive methods to stop or remove moisture, transmitting the alarm signal, stopping the chip operation, and any combinations thereof. While moisture-detecting circuitries 400, 500 of FIGS. 4 and 5, respectively, utilize analog circuitry for performing the reference Vc to actual Vc compare operation, other embodiments moisture-detecting circuitry of the present disclosure may utilize digital circuitry for performing the compare operation. Examples of digital-comparison-based moisture-detecting circuitry are described below in connection with FIGS. 6 and 7.

Figure 6:
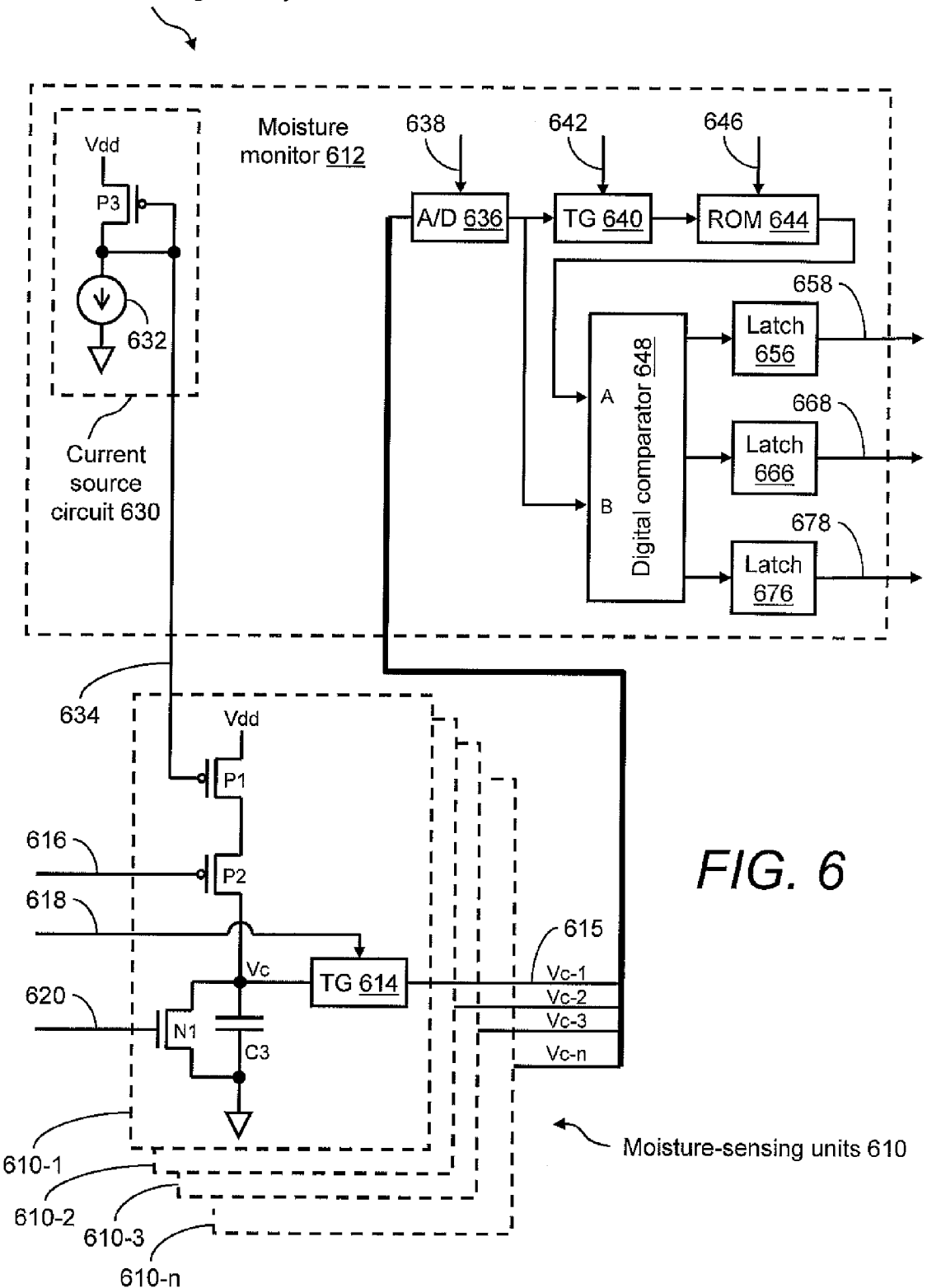
FIG. 6 is a schematic diagram of yet another example of moisture-detecting circuitry for providing a residual lifetime warning mechanism in an integrated circuit chip.

FIG. 6 shows moisture-detecting circuitry 600, which is yet another example of moisture-detecting circuitry for providing a residual lifetime warning mechanism in an IC chip (not shown). In particular, moisture-detecting circuitry 600 provides multiple levels of moisture warning and utilizes digital circuitry for performing the compare operation. Moisture-detecting circuitry 600 may include one or more moisture-sensing units 610 and a moisture monitor 612 for monitoring the states of the one or more moisture-sensing units 610. In one example, moisture-detecting circuitry 600 may include moisture-sensing units 610-1 through 610-n, as shown in FIG. 6.

The one or more moisture-sensing units 610 of FIG. 6 may be substantially the same as the one or more moisture-sensing units 410 of moisture-detecting circuitry 400 of FIG. 4, wherein each include a moisture sensing element, such as a capacitor C3, and generates a Vc sense signal 615 that is provided to moisture monitor 612. A current source circuit 630, an A/D 636, a TG 640, and a ROM 644 of moisture monitor 612 may be the same as or similar to, respectively, current source circuit 430, A/D 436, TG 440, and ROM 444 of moisture monitor 412 of moisture-detecting circuitry 400 of FIG. 4. However, moisture monitor 612 may further include a digital comparator 648 instead of an analog compare circuit. Digital comparator 648 may be, for example, a conventional A/B comparator device, wherein the A/B inputs may be one or more bits in width. Digital comparator 648 feeds one or more status latches, such as a latch 656, 666, and 678 that generate a moisture-detected signal 658, 668, and 678, respectively. In one example, when moisture-detected signal 658 is active a lowest level moisture alarm may be present, when moisture-detected signal 668 is active a moderate level moisture alarm may be present, and when moisture-detected signal 678 is active a highest level moisture alarm may be present.

The operation of moisture-detecting circuitry 600 of FIG. 6 is substantially the same as that of moisture-detecting circuitry 400 of FIG. 4 except for performing a digital compare operation instead of an analog compare operation. In particular, an initial set of reference Vc values are stored in ROM 644 to which the actual Vc values (e.g., via Vc sense signals 615) of moisture-sensing units 610-1 through 610-n are compared in a later moisture detection operation. More specifically, the output of ROM 644 feeds a first input (e.g., an A input) of digital comparator 648 and the output of A/D 636, which is the digital value of the selected Vc sense signal 615, feeds a second input (e.g., a B input) of digital comparator 648. An output of digital comparator 648 reflects whether the B input is greater or less than the A input, which is the reference Vc from ROM 644, by a predetermined amount and may trigger one or more latches 656, 666, 678 depending on the level of moisture present, as digital comparator 648 may provide multiple threshold comparison. The multiple thresholds in digital comparator 648 may be based on the following digital operations: (1) the right shift of a digital number means divided by 2, and (2) a full add operation between different bits of a digital number may generate different percentage numbers from the original. For example, if input A is a 4-bit digital number (b3 b2 b1 b0), input A may be (b3 b2 b1. b0) is A/2; input A may be (b3 b2. b1 b0) is A/4; and input A may be (b3 b2 b1. b0+b3 b2. b1 b0) is ¾ *A.

Figure 7:
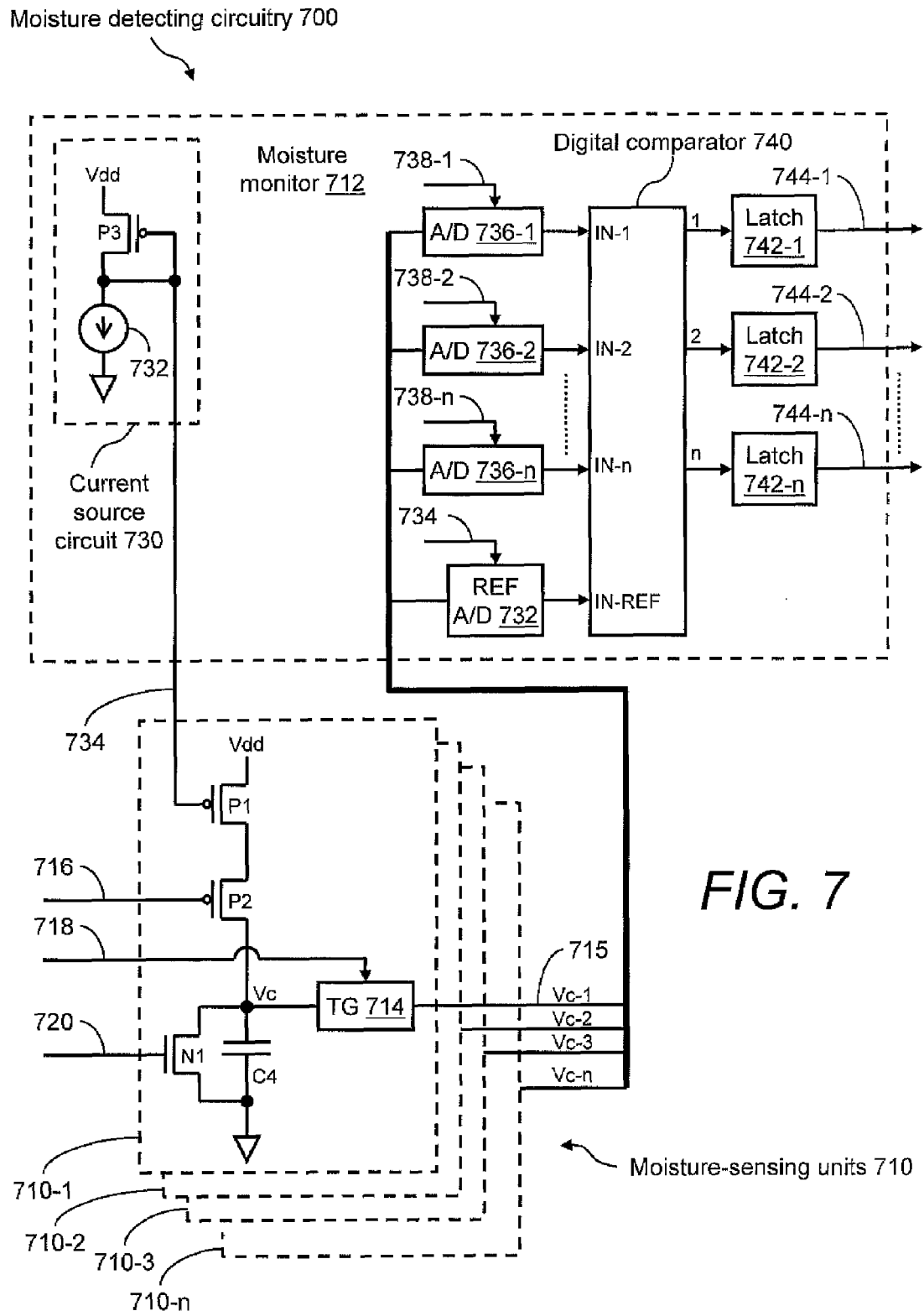
FIG. 7 is a schematic diagram of yet another example of moisture-detecting circuitry for providing a residual lifetime warning mechanism in an integrated circuit chip.

FIG. 7 shows another moisture-detecting circuitry 700, which is yet another example of moisture-detecting circuitry for providing a residual lifetime warning mechanism in an integrated circuit chip. Moisture-detecting circuitry 700 utilizes a moisture-sensing unit (which may be any one of moisture-sensing units 710-1 through 710-n depending on their layout) located at or near the geometric center of the IC chip (not show) to provide a reference Vc voltage instead of a set of stored reference Vc values for each respective moisture-sensing unit.

The one or more moisture-sensing units 710 of FIG. 7 may be substantially the same as the one or more moisture-sensing units 410 of moisture-detecting circuitry 400 of FIG. 4, wherein each includes a moisture sensing element, such as capacitor C4, and generates a Vc sense signal 715 that is connected to a moisture monitor 712, which may include a current source circuit 730 that is the same as or similar to current source circuit 430 of moisture monitor 412 of moisture-detecting circuitry 400 of FIG. 4.

Moisture monitor 712 of FIG. 7 may further include an A/D for each Vc sense signal 715-1 through 715-n, respectively. In one example, moisture monitor 712 may include A/Ds 736-1 through 736-n, having sample signals 738-1 through 738-n. Moisture monitor 712 may include a reference A/D, such as a reference (REF) A/D 732 that has a sample signal 734. Each A/D 736 and REF A/D 732 may be substantially the same as A/D 436 of moisture monitor 412 of moisture-detecting circuitry 400 of FIG. 4. The input of REF A/D 732 may be any predetermined one of the Vc sense signals 715-1 through 715-n. In one example, the input of REF A/D 732 may be the Vc sense signal 715 of the center-most moisture-sensing unit 710 of the corresponding IC chip, which may be determined upon completion of the physical layout of the IC chip.

The respective outputs of A/Ds 736-1 through 736-n feed a set of respective inputs IN-1 through IN-n of a digital comparator 740 and the output of REF A/D 732 feeds an input IN-REF of digital comparator 740. Each digital value at inputs IN-1 through IN-n is compared to input IN-REF of digital comparator 740. A set of outputs 1 through n of digital comparator 740 feed a set of latches 744-1 through 744-n, respectively. Each latch 744 may be substantially the same as latch 456 of moisture monitor 412 of moisture-detecting circuitry 400 of FIG. 4.

The operation of moisture-detecting circuitry 700 may be similar to the moisture-detecting circuitry that is described in FIGS. 4, 5, and 6, wherein the moisture sensing element, such as capacitor C4, of each moisture-sensing unit 710-1 through 710-n may be charged at the same time. When the charge is completed, A/Ds 736-1 through 736-n read the voltage Vc across the capacitors C4 via Vc sense signals 715 and the digital outputs of A/Ds 736-1 through 736-n are compared to the digital data of REF A/D 732, which may be the data of the center-most moisture-sensing unit 710 of an IC chip, at digital comparator 740. The comparison results are transmitted from digital comparator 740 to latches 744-1 through 744-n, which may be monitored for a moisture alarm status, as described in FIGS. 4, 5, and 6.

Figure 8:
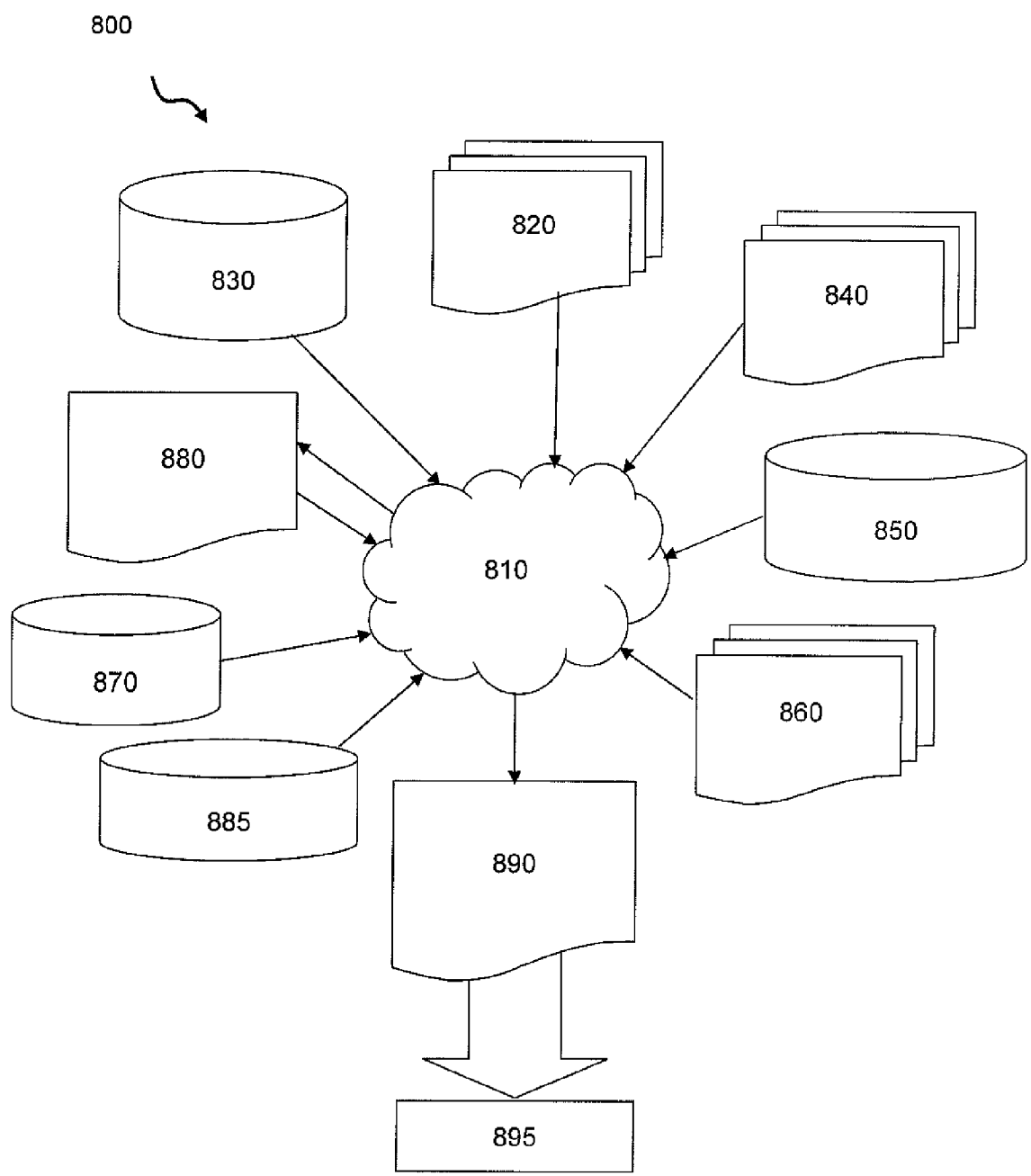
FIG. 8 is a flow diagram of a design process used in semiconductor design, manufacturing, and/or test.

FIG. 8 shows a block diagram of an example design flow 800. Design flow 800 may vary depending on the type of IC being designed. For example, a design flow 800 for building an application specific IC (ASIC) may differ from a design flow 800 for designing a standard component. Design structure 820 is preferably an input to a design process 810 and may come from an IP provider, a core developer, or other design company or may be generated by the operator of the design flow, or from other sources. Design structure 820 comprises circuit 100 in the form of schematics or HDL, a hardware-description language (e.g., Verilog, VHDL, C, etc.). Design structure 820 may be contained on one or more machine readable medium. For example, design structure 820 may be a text file or a graphical representation of circuit 100. Design process 810 preferably synthesizes (or translates) circuit 100 into a netlist 880, where netlist 880 is, for example, a list of wires, transistors, logic gates, control circuits, I/O, models, etc. that describes the connections to other elements and circuits in an integrated circuit design and recorded on at least one of machine readable medium. This may be an iterative process in which netlist 880 is resynthesized one or more times depending on design specifications and parameters for the circuit.

Design process 810 may include using a variety of inputs; for example, inputs from library elements 830 which may house a set of commonly used elements, circuits, and devices, including models, layouts, and symbolic representations, for a given manufacturing technology (e.g., different technology nodes, 32 nm, 45 nm, 90 nm, etc.), design specifications 840, characterization data 850, verification data 860, design rules 870, and test data files 885 (which may include test patterns and other testing information). Design process 810 may further include, for example, standard circuit design processes such as timing analysis, verification, design rule checking, place and route operations, etc. One of ordinary skill in the art of integrated circuit design can appreciate the extent of possible electronic design automation tools and applications used in design process 810 without deviating from the scope and spirit of the invention. The design structure of the invention is not limited to any specific design flow.

Design process 810 preferably translates an embodiment of the invention as shown in IC chip 100, along with any additional integrated circuit design or data (if applicable), into a second design structure 890. Design structure 890 resides on a storage medium in a data format used for the exchange of layout data of integrated circuits (e.g. information stored in a GDSII (GDS2), GL1, OASIS, or any other suitable format for storing such design structures). Design structure 890 may comprise information such as, for example, test data files, design content files, manufacturing data, layout parameters, wires, levels of metal, vias, shapes, data for routing through the manufacturing line, and any other data required by a semiconductor manufacturer to produce an embodiment of the invention as shown in FIG. 1. Design structure 890 may then proceed to a stage 895 where, for example, design structure 890: proceeds to tape-out, is released to manufacturing, is released to a mask house, is sent to another design house, is sent back to the customer, etc.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A design structure embodied in a machine readable medium used in a design process for an integrated circuit chip, the design structure comprising:
   functional circuitry that is located on the integrated circuit chip when the integrated circuit chip is produced; and
   moisture-detecting circuitry, which is embedded within layers of the integrated circuit chip when the integrated circuit chip is produced, that includes:
   a moisture-sensing unit for generating a sense signal that varies as a function of moisture within said moisture-sensing unit; and
   a moisture monitor in electrical communication with said moisture-sensing unit, said moisture sensing unit including:
   a memory for storing a first value, said first value stored in said memory at a first time; and
   a comparator for comparing a second value of said sense signal to said first value, said second value being provided by said moisture-sensing unit subsequent to said first value being stored in said memory.

2. The design structure of claim 1, wherein the design structure comprises a netlist, which describes the circuit.

3. The design structure of claim 1, wherein the design structure resides on a computer readable medium as a data format used for the exchange of layout data of integrated circuits.

4. The design structure of claim 1, wherein the design structure includes at least one of test data files, characterization data, verification data, or design specifications.

5. A design structure embodied in a computer readable medium for performing a method of detecting ingress of moisture into an integrated circuit chip, the design structure comprising:
   a moisture-sensing unit embedded within layers of the integrated circuit chip when the integrated circuit chip is produced, said moisture-sensing unit, when embodied in the integrated circuit chip, for generating a sense signal in response to moisture present in the integrated circuit chip;
   a means for storing a first value in a memory of the integrated circuit chip;
   a means for comparing, aboard the integrated circuit chip, a second value of said sense signal to said first value; and
   a means for generating a warning if said second value is lower than said first value by a predetermined amount.

* * * * *